United States Patent [19]

Verfaillie et al.

[11] Patent Number: 5,922,597
[45] Date of Patent: Jul. 13, 1999

[54] EX VIVO CULTURE OF STEM CELLS

[75] Inventors: Catherine M. Verfaillie; Philip B. McGlave, both of St. Paul; Jeffrey S. Miller, Little Canada, all of Minn.

[73] Assignee: Regents of the University of Minnesota, Minneapolis, Minn.

[21] Appl. No.: 08/860,866

[22] PCT Filed: Nov. 13, 1996

[86] PCT No.: PCT/US96/18222

§ 371 Date: Jul. 14, 1997

§ 102(e) Date: Jul. 14, 1997

[87] PCT Pub. No.: WO97/18298

PCT Pub. Date: May 22, 1997

Related U.S. Application Data

[60] Provisional application No. 60/006,737, Nov. 14, 1995.

[51] Int. Cl.$^6$ .............................. C12N 5/02; C12N 5/08
[52] U.S. Cl. .................................. 435/372.1; 435/372.2; 435/372.3; 435/377
[58] Field of Search ..................... 435/172.1, 172.3, 435/325, 372, 372.1, 375, 377, 366, 372.2, 372.3, 383, 384, 385, 386, 387

[56] References Cited

U.S. PATENT DOCUMENTS

| | | | |
|---|---|---|---|
| 4,883,662 | 11/1989 | Stout | 424/531 |
| 5,460,964 | 10/1995 | McGlave et al. | 435/373 |
| 5,523,286 | 6/1996 | McGlave et al. | 514/8 |
| 5,605,829 | 2/1997 | McGlave et al. | 435/377 |

FOREIGN PATENT DOCUMENTS

| | | |
|---|---|---|
| 93/18137 | 9/1993 | WIPO . |
| 93/20184 | 10/1993 | WIPO . |
| 95/13088 | 5/1995 | WIPO . |
| 96/02662 | 2/1996 | WIPO . |

OTHER PUBLICATIONS

Tamura et al., British Journal of Haematology, vol. 81, 1992, pp. 353–361.

Guido J. Tricot, Leukemia Res., vol. 16, No. 1, pp. 109–115, 1992.

*Primary Examiner*—David Guzo
*Attorney, Agent, or Firm*—Schwegman, Lundberg, Woessner, and Kluth, P.A.

[57] ABSTRACT

A method for the culture of hematopoietic cells is provided comprising culturing said cells in stromal conditioned medium comprising one or more cytokines selected from the group consisting of MIP-1α, IL-3, SCF, BB10010 and PF-4, so that the ability of the stem cells to self-replicate and differentiate is maintained or the ability of the committed progenitors to expand and differentiate is maintained.

11 Claims, 10 Drawing Sheets

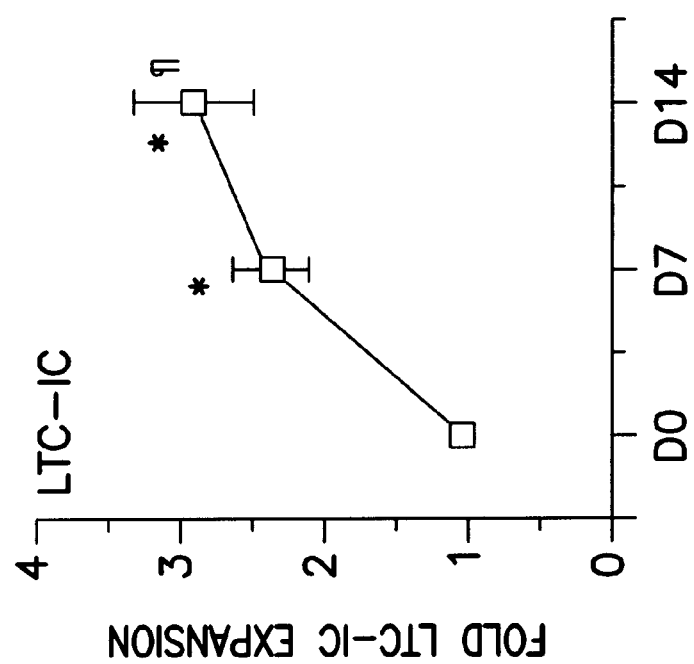
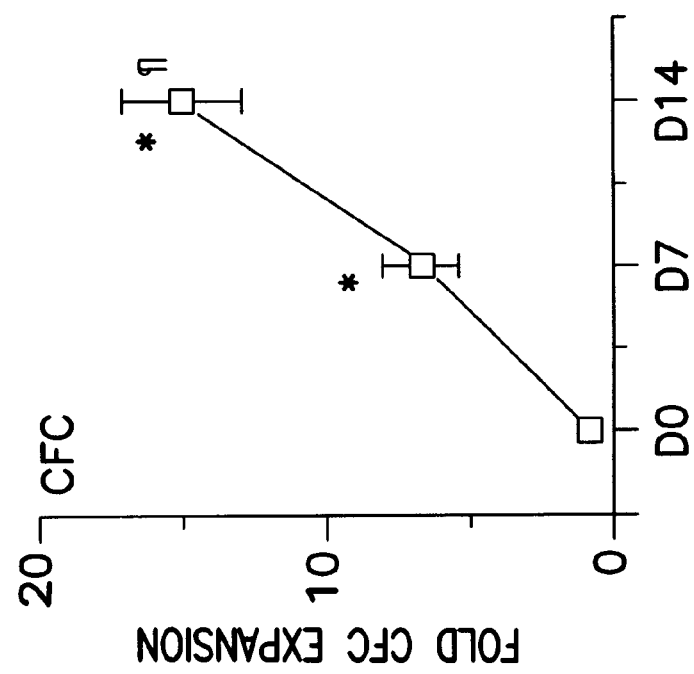
FIG. 7B
FIG. 7A

EX VIVO CULTURE OF STEM CELLS

This application is a 371 application of PCT/US96/18222, filed Nov. 13, 1996, and claims priority under 35 U.S.C. § 119(e), to U.S. provisional application Serial No. 60/006,737, filed Nov. 14, 1995 (the '737 Application). The '737 application is incorporated herein by reference.

BACKGROUND OF THE INVENTION

The human hematopoietic system is populated by cells of several different lineages. These "blood cells" may appear in bone marrow, the thymus, lymphatic tissue(s) and in peripheral blood. Within any specific lineage, there are a number of maturational stages. In most instances, the more immature developmental stages occur within bone marrow while the more mature and final stages of development occur in peripheral blood.

There are two major lineages: The myeloid lineage which matures into red blood cells, granulocyte, monocytes and megakaryocytes; and the lymphoid lineage which matures into B lymphocytes and T lymphocytes. Within each lineage and between each lineage, antigens are expressed differentially on the surface and in the cytoplasm of the cells in a given lineage. The expression of one or more antigens and/or the intensity of expression can be used to distinguish between maturational stages within a lineage and between lineages.

Assignment of cell to lineage and to a maturational stage within a cell lineage indicates lineage commitment. There are cells, however, which are uncommitted to any lineage (i.e., "progenitor" cells) and which, therefore, retain the ability to differentiate into each lineage. These undifferentiated, pluripotent progenitor cells will hereinafter be referred to as the "stem cells."

All of mammalian hematopoietic cells can, in theory, be derived from a single stem cell. In vivo, the stem cell is able to self-renew, so as to maintain a continuous source of pluripotent cells. In addition, when subject to particular environments and/or factors, the stem cells may differentiate to yield dedicated progenitor cells, which in turn may serve as the ancestor cells to a limited number of blood cell types. These ancestor cells will go through a number of stages before ultimately yielding mature cells.

The benefit of obtaining a pure population of stem cells is most readily recognized in the field of gene therapy. Gene therapy seeks to replace or repopulate the cells of the hematopoietic system which contain a defective gene with cells that do not contain the defective gene but instead contain a "normal" gene. Using conventional recombinant DNA techniques, a "normal" gene is isolated, placed into a viral vector, and the viral vector is transfected into a cell capable of expressing the product coded for by the gene. The cell then must be introduced into the patient. If the "normal" gene product is produced, the patient is "cured" of the condition. The difficulty is that the transformed cells must be capable of continual regeneration as well as growth and differentiation.

Although stem cells are potentially optimal "hosts" for transformation, substantial problems have been encountered in (a) identifying the antigenic markers unique to stem cells, (b) isolating homogenous populations comprising substantial numbers of non-lineage committed, pluripotent stem cells and (c) maintaining and, possibly, expanding populations of human stem cells.

However, a number of research groups have recently reported the isolation of populations of mammalian bone marrow cell populations which are enriched to a greater or lesser extent in pluripotent stem cells. For example, C. Verfaillie et al., *J. Exp. Med.*, 172, 509 (1990) reported that a two-step purification of low density human bone marrow cells by negative immunomagnetic selection and positive dual-color fluorescence activated cell sorting (FACS) yielded a $Lin^-/CD34^+/HLA-DR^-$ cell fraction that was 420-fold enriched in pluripotent stem cells capable of initiating long-term bone marrow cultures (LTBMC) over unmanipulated bone marrow mononucleocytes (BMMNC) obtained after Ficoll-Hypaque separation. This group reported that the combination of positive selection for small blast-like cells that are CD34 antigen positive but HLA-DR antigen negative, combined with a more extensive negative selection to deplete the population of CD2, CD19 and CD71, results in an about two- to three-fold greater enrichment in pluripotent stem cells over that Previously reported.

The development of cell culture media and conditions that will maintain stem cells in vitro for the extended periods of time required for the procedures involved in gene therapy, identification of growth factors, thorough characterization of cell morphologies and the like, has presented a unique set of obstacles. To date, successful in vitro stem cell cultures have depended on the ability of the laboratory worker to mimic the conditions which are believed to be responsible for maintaining stem cells in vivo.

For example, hematopoiesis occurs within highly dense cellular niches within the bone marrow in the adult and in similar niches within the fetal yolk sac and liver. Within these niches, stem cell differentiation is regulated, in part, through interactions with local mesenchymal cells or stromal cells. Mammalian hematopoiesis has been studied in vitro through the use of various long-term marrow culture systems. T. M. Dexter et al., in *J. Cell Physiol.*, 91, 335 (1977) described a murine system from which spleen colony-forming units (CFU-S) and granulocyte/macrophage colony forming units (CFU-GM) could be detected for several months, with erythroid and megakaryocytic precursors appearing for a more limited time. Maintenance of these cultures was dependent on the formation of an adherent stromal cell layer composed of endothelial cells, adipocytes, reticular cells, and macrophages. These methods were soon adapted for the study of human bone marrow. Human long-term culture system were reported to generate assayable hematopoietic progenitor cells for 8 or 9 weeks, and, later, for up to 20 weeks (See, S. Gartner, et al., *PNAS USA*, 77, 4756 (1980); F. T. Slovick et al., *Exp. Hematol.*, 12, 327 (1984). Such cultures were also reliant on the preestablishment of a stromal cell layer which must frequently be reinoculated with large, heterogeneous populations of marrow cells. Hematopoietic stem cells have been shown to home and adhere to this adherent cell multilayer before generating and releasing more committed progenitor cells (M. Y. Gordon et al., *J. Cell Physiol.*, 130, 150 (1987)).

Stromal cells are believed to provide not only a physical matrix on which stem cells reside, but also to produce membrane-contact signals and/or hematopoietic growth factors necessary for stem cell proliferation and differentiation. This heterogenous mixture of cells comprising the adherent cell layer presents an inherently complex system from which the isolation of discrete variables affecting stem cell growth has proven difficult. Furthermore, growth of stem cells on a stromal layer makes it difficult to recover the hematopoietic cells or their progeny efficiently.

C. M. Verfaillie, in *Blood*, 79, 2821 (1992) and P. McGlave et al., in U.S. patent application Ser. No. 07/867,814, filed Apr. 3, 1992, demonstrated that primitive, lineagenon-committed CD34$^+$/HLA-DR$^-$ cells can differentiate and can be maintained when cocultured with stromal layers but separated from the stromal layers by a 0.4 μm microporous membrane ("stroma non-contact" culture). In U.S. patent application Ser. No. 08/032,670, filed Mar. 17, 1993, P. McGlave and C. Verfaillie demonstrated that Lin$^-$/CD34$^+$/HLA-DR$^-$ cells can differentiate and proliferate when they are cultured without a stromal layer ("stroma free culture") but are supplemented daily by media conditioned by normal allogeneic bone marrow stromal layers. These studies suggest that soluble factors derived from the bone marrow stromal layers are capable of inducing differentiation of primitive human hematopoietic cells and can conserve at least a fraction of more primitive progenitors.

One role of the stromal cells in stroma-dependent cultures may be to provide a combination of cytokines that promote differentiation and proliferation of primitive hematopoietic progenitors. See, for example, E. L. W. Kittler et al., *Blood,* 12 3168 (1992) and C. J. Eaves et al., *Blood,* 78, 110 (1991). Long-term cultures can indeed be established from primitive hematopoietic progenitors in the absence of an adherent stromal layer when defined cytokines are repeatedly added. See, for example, J. Brandt et al., *J. Clin. Invest.,* 86, 932 (1990); L. W. M. M. Terstappenet ed., *Blood,* 77, 1218 (1991); G. Migliascio et al., *Blood,* 79, 2620 (1992) and D. N. Haylock et al., *Blood,* 80, 1405 (1992). Cytokines thought to be important in the induction of differentiation and/or proliferation of primitive hematopoietic progenitors are listed on Table 1, below.

TABLE 1

| Cytokine | Reference |
| --- | --- |
| rhu-G-CSF* | K. Ikebuchi et al., PNAS USA, 85, 3445 (1988) |
| rhuIL-1, rhuIL-6, | J. Brandt et al., J. Clin. Invest., 82, 1017 (1988); |
| rhuIL-3 | A.G. Leary et. al., Bood, 71, 1759 (1988) |
| rhuIL-11 | S.R. Paul et al., PNAS USA, 87, 7512 (1990); K. Tsuji et al., PNAS USA, 87, 7512 (1990) |
| LIF (leukemia inhibitory factor) | F.A. Fletcher et. al., Blood, 76, 1098 (1990) |
| SCF (stem cell factor) | J. Brandt et al., Blood, 79, 634 (1992); K.M. Zsebo et al., Cell, 63, 195 (1990) |
| bFGF | S. Huang et al., Nature, 360, 745 (1992) |
| rhuGM-CSF | J. Brandt et al., J. Clin. Invest., 86, 932 (1990) |

*rhu = recombinant human

A variety of culture systems have been described in which cells are cultured with combinations of these growth promoting cytokines in the absence of stroma-conditioned medium or stromal feeders (ex vivo cultures). For example, Haylock et al. reported that culture of mobilized peripheral blood CD34$^+$ cells with IL-1, IL-3, IL-6, G-CSF, GM-CSF and SCF increase CFU-GM by a mean of 66-fold. Haylock et al., *Blood,* 80, 1405 (1992). Additionally, Brugger et al. reported a 190-fold expansion of clonogenic progenitors following culture of mobilized peripheral blood CD34$^+$ cells with SCF, erythropoietin, IL-1, IL-3 and IL-6. Brugger et al., *Blood,* 81, 2579 (1993). However, these cultures usually do not allow expansion or even maintenance of more primitive progenitors.

The role of cytokines in the hematopoiesis occurring in long-term bone marrow cultures remains uncertain, and the factors that regulate both self-replication and the initial differentiation process of primitive uncommitted hematopoietic progenitors are still largely unknown. Therefore, there is a continuing need to characterize and evaluate factors produced by the stromal cells in long-term cultures, and to uncover and elucidate the mechanism underlying the self-replication and initial differentiation of the human hematopoietic stem cell. Characterization of such stroma-derived factor(s) may have important clinical applications, such as ex vivo stem cell expansion for use in cancer treatment and gene therapy.

SUMMARY OF THE INVENTION

The present invention provides a method for the long-term culture of mammalian, preferably murine or human, hematopoietic cells. As used herein, the term "hematopoietic cells" includes both the uncommitted, pluripotent "stem cells" described above, as well as the lineage-committed, or dedicated, progenitor cells which can develop into mature "blood cells" and mixtures thereof. Thus, the present method is effective to maintain the stem cell population in a population of hematopoietic cells such as the Lin$^-$/CD34$^+$/HLA-DR$^-$ marrow cell population and the less selected CD34$^+$ enriched population described above. The ability of the present method to maintain and/or expand the population of stem cells within a cell population can be evaluated by determining the continuing presence/number of cells capable of initiating long-term bone marrow cultures (LTC-IC) as disclosed hereinbelow. The presence of these cells after at least 5–8 weeks of culturing a given population of cells provides art-recognized confirmation that stem cells have been preserved and/or expanded.

One embodiment of the present method comprises maintaining a population of hematopoietic cells in a fixed, non-contacting relationship to a population of cultured mammalian stromal cells, i.e., human or murine stromal cells or cell lines, which populations are preferably in liquid stromal cell growth medium connection during culturing. For example, the stromal cell population and the hematopoietic cell population may be adhered to, or supported by, discrete cell culture substrata, which substrata are immersed in a stationary or flowing body of stromal cell culture medium.

Preferably, the medium contains an amount of a cytokine effective to maintain and/or expand the LTC-IC and CFC present in the population. It is further preferred that this cytokine be chosen from the group consisting of IL-3, SCF, PF4, MIP-1α and BB10010.

A preferred embodiment of the present invention comprises a method for the long-term, ex vivo culture of hematopoietic cells. Specifically, the method comprises maintaining a population of hematopoietic cells in a stromal-conditioned medium, in the absence of a population of cultured mammalian stromal cells. As used herein, the term "stromal conditioned medium" is meant to indicate medium that has been exposed to stromal cells, and the stromal cells removed subsequent to said exposure.

It is preferred that the medium comprises an effective amount of one or more cytokines. The amount of the cytokine or combination thereof that is present is that amount sufficient to maintain and/or expand the LTC-IC and CFC present in said hematopoietic cell population. It is further preferred that this cytokine be chosen from the group consisting of IL-3, SCF, PF4, MIP-1α and BB10010. It is further preferred that the hematopoietic cell populations are both human and allogeneic, most preferably they are autologous, although they need not be.

The present method is also effective to derive and expand committed progenitors both from such hematopoietic cell populations, as well as from already committed progenitor cells, such as those from sources such as human bone marrow, human newborn cord blood, fetal liver and adult human peripheral blood. The existence and number of committed progenitors can be determined by assaying for colony-forming cells (CFC) as disclosed hereinbelow. Preferably, the populations are both human and allogeneic, most preferably they are autologous, although they need not be. Thus, a bioactive essentially homogeneous population of cells, prepared by the aforementioned method is also within the scope of the present invention.

Thus, the present method at least substantially conserves the stem cell population throughout the culturing period, while preserving, and preferably enhancing, its ability to differentiate into lineage-committed progenitor cells hereinafter referred to as "committed progenitors"). The present method can also be used to derive and be used to derive and expand committed progenitors (CFC) from already committed progenitor cell populations. As used herein, the term "stromal cells" includes (1) human allogeneic or autologous stromal cells, or non-human stromal cells,
(2) human or non-human stromal cell lines which need not be hematopoietic, and
(3) human or non-human virally infected cell lines, such as immortalized embryonic fibroblasts which are effective to provide "feeder layers" for stem cell populations.

Unless stated otherwise, molecular weights given below were determined by SDS-PAGE under reducing conditions.

BRIEF DESCRIPTION OF THE DRAWINGS

FIG. 6A depicts the assay for CFC in methylcellulose progenitor culture and FIG. 6B depicts the assay for LTC-IC utilizing a limiting dilution assay.

FIGS. 7A and 7B are graphs that depict the scaled up culture of DR– cells with SCM+IL-3 results in significant CFC and LTC-IC expansion. Specifically, FIG. 7A depicts the assay for CFC in methylcellulose progenitor culture and FIG. 7B depicts the assay for LTC-IC utilizing a limiting dilution assay.

FIG. 9 (Parts A–B) is a graphical depiction that illustrates the expansion of CFC and LTC-IC from CML DR⁻ cells following SCM+IL-3 culture. Specifically.

DETAILED DESCRIPTION OF THE INVENTION

Figure 1:
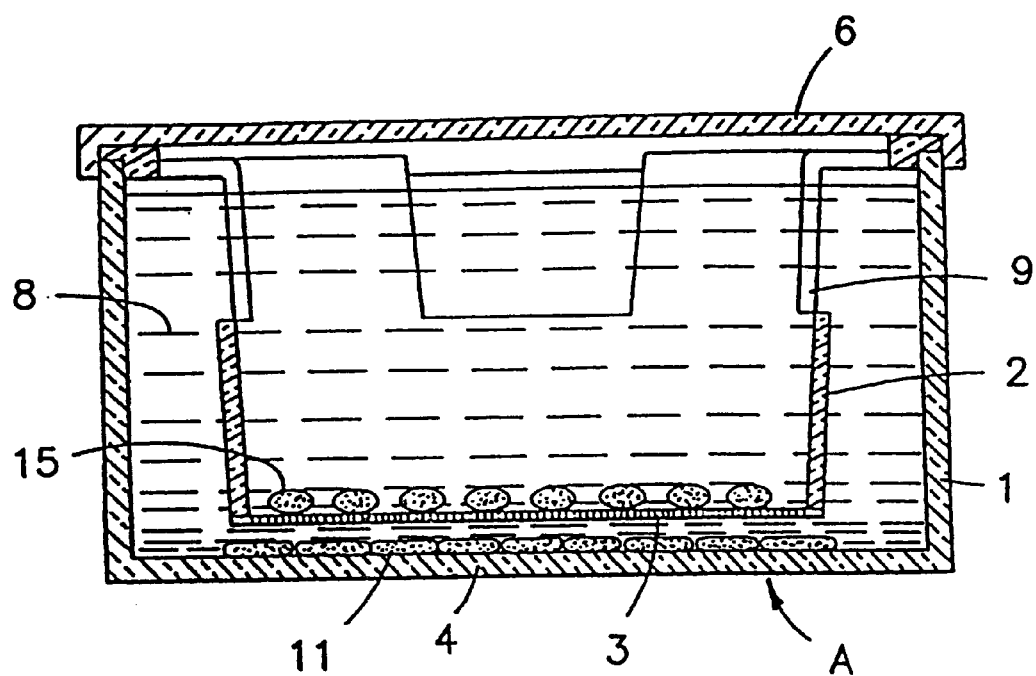
FIG. 1 is a schematic cross-sectional view of a cell culture chamber useful in strom-non-contact cultures.

A. Isolation of Hemlatopoietic Cells Enriched with Stem Cells

The stem cell population constitutes only a small percentage of the total number of leukocytes in bone marrow. Additionally, at the present time, antigens present on stem cells alone or which are also present on more differentiated progenitors have not been fully identified. As in mice, one marker which has been indicated as present on human stem cells, CD34, is also found on a significant number of lineage committed progenitors. Another antigen which provides for some enrichment of progenitor activity is Class II HLA (particularly a conserved DR epitope recognized by a monoclonal antibody designated J1-43). However, these markers are also found in numerous lineage committed hematopoietic cells. The Thy-1 molecule is a highly conserved protein present in the brain and in the hematopoietic system of rat, mouse and man. These species differentially express this antigen and the true function of this molecule is unknown. However, the Thy-1 molecule has been identified on rat and mouse hematopoietic stem cells. This protein is also believed to be present on most human bone marrow cells, but may be absent on stem cells.

Isolation of populations mammalian bone marrow cell populations which are enriched to a greater or lesser extent with pluripotent stem cells can be achieved through the use of these and other markers. For example, monoclonal antibody My-10, which is found on progenitor cells within the hematopoietic system of non-leukemic individuals, is expressed on a population of progenitor stem cells recognized by My-10 (i.e., express the CD34 antigen) and can be used to isolate stem cells for bone marrow transplantation. See Civin, U.S. Pat. No. 4,714,680. My-10 has been deposited with the American Type Culture Collection (Rockville, Md.) as HB-8483 and is commercially available from Becton Dickinson Immunocytometry Systems ("BDIS") as anti-HPCA 1. However, since using an anti-CD34 monoclonal antibody alone is not sufficient to distinguish between "stem cells," and the true pluripotent stem cell (B cells (CD19⁺) and myeloid cells (CD33⁺) make up 80–90% of the CD34⁺ population), a combination of monoclonal antibodies must be used to select human progenitor stem cells.

For example, a combination of anti-CD34 and anti-CD38 monoclonal antibodies can be used to select those human progenitor stem cells that are CD34⁺ and CD38⁻. One method for the preparation of such a population of progenitor stem cells is to stain the cells with immunofluorescently labeled monoclonal antibodies. The cells then may be sorted by conventional flow cytometry with selection for those cells that are CD34⁺ and those cells that are CD38⁻. Upon sorting, a substantially pure population of stem cells results. (Becton Dickinson Company, published European Patent Application No. 455,482)

Additionally, negative selection of differentiated and "dedicated" cells from human bone marrow can be utilized to yield a population of human hematopoietic stem cells with fewer than 5% lineage committed cells. See Tsukamoto et al., U.S. Pat. No. 5,061,620. The stem cells that result are characterized as being CD34⁺, CD3⁻, CD7⁻, CD8⁻, CD10⁻, CD14⁻, CD15⁻, CD19⁻, CD20⁻, CD33⁻, Class II HLA⁺ and Thy-1⁺.

Furthermore, a two-step purification of low density human bone marrow cells by negative immunomagnetic selection and positive dual-color fluorescence activated cell sorting (FACS) can be used to yield a Lin⁻/CD34⁺/HLA-DR⁻ cell fraction that is 420-fold enriched in pluripotent stem cells capable of initiating long-term bone marrow cultures (LTBMC) over unmanipulated bone marrow mononucleocytes (BMMNC) obtained after Ficoll-Hypaque separation. See C. Verfaillie et al., *J. Exp. Med.* 172, 509 (1990) (Hereinafter C. Verfaillie et al.). The combination of positive selection for small blast-like cells that are CD34 antigen positive but HLA-DR antigen negative, combined with a more extensive negative selection to deplete the population of CD2, CD19 and CD71, results in an about two- to three-fold greater enrichment in pluripotent stem cells over that previously reported.

B. Autologous transplantation

Relapse of the underlying disease due to contamination of the autograft with malignant cells and/or the persistence of malignant cells within the host following myeloblative therapy continue to be the major causes of failure following autologous transplantation. Selection of populations enriched for primitive progenitors such as $CD34^+HLA-DR^-$ cells ($DR^-$ cells), $CD34^+Thy_1^{low}$ cells and $CD34^+CD38^-$ cells, are a potential source of benign stem cells suitable for autografting in patients with various malignancies such as chronic myelogenous leukemia (CML), lymphoma, multiple myeloma and breast cancer. Verfaillie et al., *Blood,* 79, 1003 (1992).

However, it may not be possible to select sufficient numbers of DR– cells in certain patients. In addition, selection of DR– cells, which are enriched in primitive progenitors, is associated with depletion of committed progenitors. Srour et al., *Blood,* 82, 3333 (1993). Several studies suggest that committed progenitors may be responsible for initial, unsustained engraftment following transplantation whereas primitive progenitors may produce delayed but durable engraftment. Verfaillie et al., *J. Exp. Med.,* 179, 509 (1990). However, other studies have indicated that primitive progenitor populations may be important for both the early phase of hematopoietic recovery as well as sustained hematopoiesis following transplantation. Uchida et al., *Blood,* 88, 3758 (1994). Therefore, the use of DR– cells for autologous BMT requires the use of an ex vivo culture system that is capable of expanding both committed progenitors and more primitive progenitors.

C. Culture of Hematopoietic Cells in a "Stroma Non-Contact" System

In the "stroma non-contact" system, the hematopoietic cell population is physically supported by a culture substratum such as a microporous hollow fiber on a microporous membrane which maintains the hematopoietic cells and any associated cells in contact with a liquid culture medium. The pores of the membrane or the hollow fibers can vary in size, so long as they allow culture medium and its components to contact the hematopoietic cells, while providing adequate support for the cells. Preferably, the microporous membrane or the hollow fibers are formed of a synthetic polymer, which can be coated with a cell-adherence promoting peptide, such as mammalian (human) collagen, laminin, fibronectin or the subunits thereof possessing the ability to promote hematopoietic cell attachment. For example, such peptides are disclosed in U.S. Pat. Nos. 5,019,546, and 5,059,425.

The hematopoietic cells may be attached to the interior of a microporous tube or hollow fiber, while the stromal cells are maintained in a fixed relationship from the exterior of the tubing, e.g., on the walls of a chamber containing the growth medium.

During culture, the liquid growth medium may be held as a stationary body which envelops both populations of cells, and is preferably about 25–100% exchanged at fixed intervals, e.g., of 8 hrs.–14 days, preferably of about 1–10 days. Alternatively, the culture medium can be continuously circulated through a culture chamber that contains the hematopoietic cells and replaced/replenished at a site remote from the culture chamber.

One commercially-available device suitable for use in a stroma-non-contact system is the Transwell™ series of cell culture chambers available from Costar Corp., Cambridge, Ma., U.S.A. As depicted in schematic cross-section in FIG. 1, each Transwell® chamber (A) comprises a flat-bottomed plastic lower compartment 1, and a plastic upper compartment 2, which can be removably inserted into compartment 1, so that the collagen-coated, microporous membrane 3 (0.45 μm pore diameter), which forms the bottom of compartment 2, is held in a fixed, essentially parallel relationship to the inner surface of the bottom (4) of the compartment. This assembly is covered by a removable lid 6. In use, a preselected amount of liquid culture medium 8 is added to the lower compartment 1. Stem cells or other hematopoietic cells 15 are added to the upper surface of microporous membrane 3 and the upper compartment (or transwell) 2 is inserted into the lower compartment. Opening 2 in the sidewall of the transwell 2 permits addition of or removal of the medium 8 from the exterior void space of the chamber A. The cover 6 is then replaced. Following the culture period, which can be as long as 3–6 months, the cover 6 is removed; the transwell is removed, and all or a portion of the cells 15 are then removed from the microporous membrane and employed in the end use.

D. Ex Vivo Culture of Hematopoietic Cells

Culture in the above mentioned stroma non contact system results in enhanced LTC-IC maintenance as well as enhanced committed progenitor generation. Similar results are obtained when $DR^-$ cells ware cultured in medium conditioned by stromal feeders present in a separate culture vessel, indicating that factors required for maintenance of primitive progenitors and limited differentiation to more committed myeloid progenitors are all present in stromal supernatants. Therefore, it was determined that stromal conditioned medium (SCM) may be used in place of stromal feeders for ex vivo expansion of primitive progenitors.

The advantage of using SCM in clinical expansion cultures rather than stromal feeders is its simplicity and the relative ease with which it can be adapted for clinical use. SCM cultures obviate the need for continuous perfusion a stromal feeder during progenitor culture. In addition, SCM can be collected prior to progenitor culture and batch tested for quality assurance. Finally allogeneic or even xenogeneic stromal feeders can be used to generate SCM which may be superior to autologous stromal feeders derived from patient marrow. See, Bhatia et al., *Blood,* 8, 3636 (1995).

As used herein, "stromal conditioned medium" is meant to indicate medium that has been exposed to stromal cells; said stromal cells being removed subsequent to said exposure. One method of preparing SCM is disclosed hereinbelow.

Additionally, it has now been discovered that an ex vivo culture system employing the combination of SCM with a single cytokine, IL-3, can achieve expansion of committed progenitors without loss, but rather expansion of primitive progenitors and at least maintenance of lymphoid potential. PF4, MIP-1α and BB10010 (a variant of MIP-1α) further enhanced LTC-IC expansion in SCM and IL-3 cultures without increasing CFC expansion, confirming that enhanced maintenance/expansion of LTC-IC may result from the combined inhibitory effects of SCM and these chemokines on primitive progenitor exhaustion. Verfaillie et al., *Blood,* 86, 2137 (1995). Interestingly, addition of SCF to SCM+IL-3 cultures resulted in further expansion of both committed progenitors and LTC-IC. Since selection of the DR$^-$ subpopulation of CD34$^+$ cells results in 5–10 fold depletion of committed progenitors (See, Verfaillie et al., *J. Exp. Med.,* 179, 509 (1990), the 5–10 fold CFC expansion achieved in this culture system compensates for the loss of committed progenitors associated with selection of the DR– primitive progenitor population.

It was also discovered that BCR/ABL mRNA negative progenitors present in DR$^-$ cells selected from CML BM were also expanded in this culture system. Therefore, this culture system could be adapted to the expansion of selected primitive progenitor populations prior to autologous transplantation.

The invention will be further described by reference to the following detailed examples.

Marrow samples

Human bone marrow was obtained from 22 healthy young volunteers or from chronic phase chronic myelogenous leukemia patients after informed consent by aspiration from the posterior iliac crest in preservative free heparin. Bone marrow mononuclear cells (BMMNC) were isolated by Ficoll-Hypaque (Sigma Diagnostics, St. Louis, Mo.) density gradient separation (specific gravity 1.077) for 30 minutes at 37° C. and 400 g.

Cytokines

The following cytokines were used in the examples hereinbelow, at the concentrations indicated: interleukin-3 (IL-3) (5–50 ng/ml), interleukin-7 (IL-7) (10 ng/ml), macrophage inflammatory protein-1α (MIP-1α) (100 ng/ml) (R&D, Minneapolis, Minn.), platelet factor-4 (PF-4) (200 ng/ml) (a gift from Dr Arne Slungaard, Minneapolis, Minn.) interleukin-6 (IL-6) (10 ng/ml) and interleukin-11 (IL-11) (10 ng/ml) (gifts from Dr. M. Linesky, Genetics Institute, Boston, Mass.), interleukin-1 (IL-1) (50 u/ml) (a gift from Dr. M. B. Widmer, Immunex Biologicals, Seattle, Wash.), granulocyte-macrophage colony stimulating factor (GM-CSF) (50 u/ml) (Immunex Biologicals), granulocyte-colony stimulating factor (G-CSF) (5ng/ml) (Amgen, Thousand Oaks, Calif.), stem cell factor (SCF) (10 ng/ml) (a kind gift from Dr. K. Langley, Amgen) and BB-10010 (100 ng/ml) (a kind gift from Dr. Lloyd Czaplewski, British Biotech Pharmaceuticals, Ltd, Oxford, UK).

Preparation of stromal conditioned medium

Bone marrow stromal layers were established in T-75 or T-150 flasks by culturing normal BMMNC in LTBMC medium, described in Example 2, "Stroma-Free cultures", hereinbelow. A complete medium change was done five days after initiating the cultures and half medium changes were subsequently done every week. Confluent stromal layers formed after 4 to 5 weeks of culture and were irradiated at 1,250 cGy using a Cesium irradiator to eliminate endogenous hematopoiesis. A complete medium change was done the day following irradiation, following which half of the medium conditioned by the stromal was collected every two to three days and replaced with fresh LTBMC medium for a total of two weeks. The stroma-conditioned medium (SCM) was centrifuged at 1000 g for 10 minutes to remove suspended cells and filtered through a 0.451 μm pore filter with low protein binding (Sterivex-HV, Millipore Corp., Bedford, Mass.). SCM was stored at −20° C. until it was used.

Methylcellulose assay

Cultured hematopoietic cells were assayed in the short term methylcellulose assay for the presence of committed progenitors. In the short-term methylcellulose assay, the Lin$^-$/CD34$^+$/HLA-DR$^-$ cells were plated in clonogenic methylcellulose assay supplemented with 3 IU recombinant erythropoietin (Epoetin) (Amgen, Thousand Oaks, Calif.) and 5% conditioned media from the bladder carcinoma cell line 5637 (American Tissue Type Culture Collection, [ATCC], Rockville, Md.) as described by C. Verfaillie et al. Cultures were incubated in a humidified atmosphere at 37° C. and 5% CO$_2$ for 14–18 days. The cultures were assessed at day 14–18 of culture for the presence of CFU-MIX, granulocyte/macrophage colony forming units (CFU-GM) and erythroid burst-forming units (BFU-E) as described by C. Verfaillie et al.

Limiting dilution assays

To carry out limiting dilution assays (LDA) for LTC-IC, at day zero Lin$^-$/CD34$^+$/HLA-DR$^-$ cells were plated in limiting dilutions on M2-10 B4 murine fibroblast feeders (a gift from Dr. C. J. Eaves, Terry Fox Laboratories, Vancouver Canada) subcultured in 96 well plates (300, 100, 33 or 11 cells/well; 22 replicates per concentration). See H. J. Sutherland et al., *Blood,* 7, 666 (1991) and *PNAS USA,* 87, 2584 (1990). Cultures were maintained in a humidified atmosphere, at 37° C. and 5% CO$_2$ for 5 weeks. Cultures were fed at weekly intervals by removal of half the medium from the wells and replacement with fresh medium. At week 5, all medium was removed from the wells and they were overlaid with methylcellulose progenitor medium, as described above and wells were evaluated for the presence of committed progenitors. The absolute number of LTC-IC present in the different cell populations was calculated as the reciprocal of the concentration of test cells that gave 37% negative cultures using the Poisson statistics (E. H. Porter et al., *J. Cancer,* 17, 583 (1963)) and the weighted mean method (C. Taswell, *J. Immunol.,* 126, 1614 (1981)).

Statistical Analysis

Results of experimental points obtained from multiple experiments were reported as the mean±standard error of the mean (SEM). Significance levels were determined by two-sided students t-test analysis.

EXAMPLE 1

Selection of Progenitors

Bone marrow mononuclear cells (BMMNC) were purified further in an initial counterflow elutriation step, by suspending BMMNC in phosphate buffered saline (PBS) supplemented with 0.3% bovine serum albumin (BSA) (Sigma) and 0.01% ethylene diamine tetraacetic acid (EDTA) (Sigma). The cells were injected into an elutriator system with standard separation chamber (Beckman Instruments, Inc., Palo Alto, Calif.) primed with Iscove's Modified Dulbecco's Medium (IMDM), 5% fetal calf serum (FCS) and 0.01% EDTA. Rotor speed and temperature were maintained at 1,950 RPM and 10° C. After loading, 200 ml of effluent was collected at a flow rate of 14 ml/min. The rotor was then stopped and the remaining BMMNC flushed from the separation chamber. Cells collected in fraction 14 were then depleted from T-lymphocytes and NK cells by sheep erythrocyte rosetting as described by C. M. Verfaillie et al., *Blood,* 77, 263 (1991). Further depletion of committed lymphoid and myeloid/monocytic cells was obtained by negative immunomagnetic depletion of cells expressing CD2, CD3, CD11b, CD19, CD56, CD71, MY8 and glycophorin-A antigens using the methods described in C. Verfaillie et al.

The resultant lineage negative (Lin$^-$) cells were labeled with anti-CD34 and anti-HLA-DR antibodies as described by C. Verfaillie et al. Cells were sorted on a FACS-Star-Plus laser flow cytometry system (Becton-Dickinson, Mountain View, Calif.) equipped with a Consort 40 computer. Cells were initially selected for low vertical and very low/low horizontal light scatter properties. Cells selected in the first window expressing high numbers of CD34 antigens and lacking HLA-DR antigen expression were then sorted to yield Lin$^-$/CD34$^+$/HLA-DR$^-$ cells, as described by C. Verfaillie, et al. These Lin$^-$/CD34$^+$/HLA-DR$^-$ cells correspond to the highly stem cell-enriched population designated as Lin$^-$34$^+$DR$^-$ in C. Verfaillie et al. The latter windows were chosen on the basis of the fluorescence pattern of control samples labeled with mouse IgG1-PE and mouse IgG2a-FITC antibodies.

EXAMPLE 2

In vitro Culture of DR$^-$ Stem Cells

The DR$^-$ cells were cultured as follows:

1. "Stroma-Free" cultures: 2–8×10$^3$/ml DR$^-$ cells were plated in complete media in wells of 24 (1 ml) or 6 well plates (4 ml) (Costar, Cambridge, Mass.). No stromal layers were established. No cytokines were added to the complete media. The culture media consisted of IMDM with 12.5% fetal calf serum (HyClone Laboratories, Logan, Utah), 12.5% horse serum (HyClone Laboratories, Logan, Utah), 2 mM L-glutamine (Gibco Laboratories), penicillin 1,000 U/m, streptomycin 100 U/ml (Gibco) and 10$^{-6}$ hydrocortisone (A-Hydrocort) (Abbot Laboratories, North Chicago, Ill.).

2. "Stroma-contact" cultures: Irradiated stromal cells were subcultured in 6 well (2×10$^6$ cells suspended in 4 ml) or 24 well (0.5×10$^6$ cells suspended in 1 ml) plates. DR$^-$ cells (2–8×10$^3$/ml) were then plated onto the irradiated allogeneic stromal layers.

3. "Stroma-non-contact" cultures: "Transwell" cultures consisted of allogeneic irradiated stromal cells derived from the same donors as the stromal cells used in the "stroma-contact" cultures subcultured in the bottom well of 6 well (2×10$^6$ cells suspended in 3 ml) or 24 well (0.5×10$^6$ cells suspended in 0.8 ml) "Transwell" plates. A collagen treated transwell insert (0.45 µm microporous filter)(Costar) was then placed on top of the stomal layer, and sorted DR$^-$ cells plated in the upper wells (2–8×10$^3$ cells in 0.2 ml complete media for 24 well plates, or 4–32×10$^3$ DR$^-$ cells in 1 ml complete media for 6 well plates).

4. Maintenance of cultures: All cultures were maintained in a humidified atmosphere at 37° C. and 5% CO$_2$. At weekly intervals "stroma-contact" and "stroma-free" cultures were fed by removing half of the cell-free supernatant and replacing it with fresh complete media. For "stroma-non-contact" cultures, half the media from the bottom wells only was removed and replaced by fresh complete media.

5. Evaluation of long-term cultures: Non-adherent and adherent cells recovered from selected "stroma-contact" cultures after treatment with 0.15% collagenase (Boehringer Mannheim) were assayed at different time points in the short term methylcellulose assay for the presence of committed progenitors, as described hereinabove.

Likewise, cells from selected "stroma-free" cultures or present in the upper wells of selected "stroma-non-contact" cultures were collected at different time points, enumerated under a hemocytometer, examined for their morphology and phenotype and assayed for the presence of committed or primitive progenitors. To determine phenotype, cells collected from the upper wells of "Transwell" cultures were analyzed at week 5 of culture for the presence of CD34$^+$/HLA-DR$^+$ and CD34$^+$/HLA-DR$^-$ cells. Cells were labeled with anti-CD34-PE antibody (Becton-Dickinson) and anti-HLA-DR-FITC antibody (Becton-Dickinson). Cells were analyzed for the expression of these antigens on a FACS-Star-Plus flow cytometry system, equipped with a Consort computer. PE and FITC coupled isotype-matched mouse immunoglobulins were used as controls.

Limiting dilution assays were carried out basically as described above, with the following alterations in protocol. Specifically, at day zero DR$^-$ cells (24 replicates per concentration)(experiment 1–3: 1000, 333, 111 or 33; experiment 4: 500, 200, 100 or 20; experiment 5–6: 400, 150, 50, 15 DR$^-$ cells/well) were plated onto 3×10$^4$ irradiated allogeneic stromal cells subcultured in 96 well plates (Costar) (day-0 limiting-dilution assay=LDA). See H. J. Sutherland et. al., *Blood*, 78, 666 (1991) and *PNAS USA*, 87, 2584 (1990). Likewise, cells recovered after 5 weeks from collagenase treated "stroma-contact" cultures or transwell-inserts of "stroma-non-contact" cultures initiated at day 0 with 35,488 (experiments 1–3), 19,680 (experiments 4–6) or 14,760 (experiments 5–6) DR$^-$ cells were plated in LDA (cell number=the equivalent of 1,000, 333, 111 and 33 (experiments 1–3), 500, 200, 100 or 20 (experiment 4) or 400, 150, 50, 15 (experiments 5–6) DR$^-$ cells at day 0; 23±1 replicates per concentration). Stromal layers used to perform LDA at day 0 and at day 35 after initial culture in "stroma-contact" or "stroma-non-contact" cultures were derived from bone marrow samples from the same allogeneic donor.

DR$^-$ cells were suspended in fetal calf serum, horse serum and hydrocortisone containing media but without exogenous cytokines. Cell suspensions were plated either without stromal layer ("stroma-free"), directly onto allogeneic irradiated stromal layers ("stroma-contact") or in transwell-inserts which separated DR$^-$ cells from the stroma by a 0.45 µm microporous collagen-coated membrane allowing free passage of diffusible factors by preventing cell-cell contact ("stroma-non-contact") as shown in FIG. 1. These translucent transwell inserts were placed one mm above the stromal layer which was adherent to the bottom well but remained completely separated from the transwell insert throughout the culture period. Repeated visual inspection demonstrated that no adherent stromal layer was formed in "stroma-free" cultures nor in the transwell inserts of "stroma-non-contact" cultures.

Figures 2A, 2B:
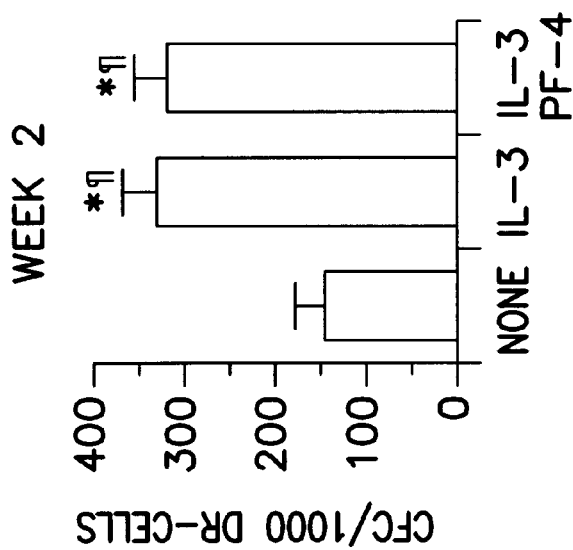
FIG. 2 (Parts A–C) is a graphical depiction of the CFC expansion of DR cells in a culture of stromal conditioned media+IL-3, and a culture of stromal conditioned media+IL-3 and PF4.

When DR$^-$ cells were plated in the absence of a stromal layer ("stroma-free"), a progressive decline in cell number is observed (FIG. 2A). Virtually all cells were monocytes at week 2. In contrast, serial evaluation of "stroma-non-contact" cultures revealed that, after an initial decline in cell number at week 1, the cell number in the transwell-inserts increased steadily (FIG. 2B). At week 1, more than 55% of cells were blasts admixed with promyelocytes. Over the next 4 weeks, the percentage of blasts declined; the percentage of promyelocytes remained constant and a gradual increase in mature myeloid elements was seen. At week 8, blasts and myeloid precursors decreased further with a reciprocal increase in monocytes. FACS analysis of cells present in "stroma-non-contact" cultures at week 5 demonstrated that 4.1±1.2% of cells were CD34$^+$/HLA-DR$^+$ (n=6) associated with more differentiated hematopoietic progenitors, and 1.1±16% of cells remained CD34$^+$/HLA-DR$^-$ (n=6). Taking into account that the total cell number was 8±3.8 fold higher at week 5 compared with day 0, these studies demonstrate that for each DR$^-$ cell used to initiate the cultures 19±5 CD34$^+$/HLA-DR$^+$ cells were generated and approximately 6% of DR$^-$ cells could be conserved for a minimum of 5 weeks.

These experiments demonstrate that, although stroma is important for in vitro hematopoiesis, direct contact between stem cells and the stromal layer is necessary neither for the differentiation of such progenitors into more differentiated $34^+/DR^+$ cells and mature myeloid cells, nor for the conservation of a fraction of primitive $34^+/DR^-$ progenitors.

To test this hypothesis further, cells recovered from "stroma-free", "stroma-contact" and "stroma-non-contact" were plated in cultures in the methylcellulose progenitor assay to evaluate the production of clonogenic cells. As demonstrated by the data summarized in Table 2, very few clonogenic cells were present in "stroma-free" cultures during the first 3 weeks, while none were present in such cultures at weeks 5 and 8.

TABLE 2

Recovery of committed progenitors from primitive
DR cells cultured in "stroma-free," "stroma-non-contact"
and "stroma-contact" cultures.

| Culture | Week (n =) | No. of Colonies per 5,000 DR$^-$ Cells$^a$ | | |
|---|---|---|---|---|
| | | CFU | CFU-GM | BFU-E |
| Sorted DR$^-$ Cells | 0(5) | 66.4 ± 13.9 | 25.5 ± 1.65 | 40.9 ± 12.6 |
| "Stroma-free" | 1(3) | 12.2 ± 5.1 | 8.8 ± 1.8 | 3.3 ± 3.3 |
| | 2(4) | 4.2 ± 3.2 | 1.8 ± 1.2 | 2.5 ± 2.5 |
| | 3(2) | 13.3 ± 0 | 13.3 ± 0 | 0 ± 0 |
| | 5(4) | 0 ± 0 | 0 ± 0 | 0 ± 0 |
| | 8(2) | 0 ± 0 | 0 ± 0 | 0 ± 0 |
| "Stroma-contact" | 1(4) | 81.7 ± 10 | 39.3 ± 8.1 | 45.3 ± 9.9 |
| | 2(5) | 85.8 ± 17.7 | 53.7 ± 12.1 | 35.7 ± 7.7 |
| | 3(2) | 96.3 ± 23.3 | 58.3 ± 15 | 38.3 ± 8.3 |
| | 5(12) | 150 ± 16.7 | 108 ± 23 | 44.1 ± 9.8 |
| | 8(2) | 47.8 ± 1.8 | 34.95 ± 1.65 | 13.3 ± 3 .3 |
| "Stroma-non-contact" | 1(4) | 107.5 ± 15* | 8.88 ± 8.8* | 25.4 ± 4.2 |
| | 2(5) | 126.8 ± 30* | 86.4 ± 28.8* | 31.8 ± 9.7 |
| | 3(2) | 165.7 ± 79 | 154 ± 74 | 9.5 ± 2.5 |
| | 5(12) | 333 ± 41$^{\dagger *}$ | 273 ± 37$^{\dagger *}$ | 28.3 ± 9.8* |
| | 8(2) | 99.6 ± 19.6* | 98 ± 18$^{\dagger *}$ | 1.6 ± 1.6 |

$^a$Colonies were enumerated at day 14–19 (CFC = colony forming cells; CFU-GM = granulocyte-macrophage colony-forming-unit; BFU-E = erythroid burst-forming unit). Results are the mean number ± SEM of colonies obtained from 5,000 DR cells. (x) = values between brackets represent the number of experiments.
Students t-test: *$p \leq 0.01$; comparison between "stroma-free and "stroma-non-contact" cultures.
$^\dagger = p \leq 0.01$; comparison between "stroma-contact" and "stroma-non-contact" cultures.

"Stroma-contact" cultures yielded an increasing number of clonogenic cells over the first 5 weeks with a decrease in committed progenitor recovery by week 8. When DR$^-$ cells were plated in "stroma-non-contact" culture, a similar increase was observed in the generation of committed progenitors during the first 5 weeks, which declined by week 8. These studies demonstrated that bone marrow derived stromal cells are required for the proliferation and differentiation of primitive hematopoietic progenitors when no exogenous cytokines are provided. However, induction of differentiation does not require direct contact between the hematopoietic progenitors and the stromal layer, suggesting that diffusible factors are released from the stromal environment that induce differentiation of primitive progenitors placed in a transwell-insert 1 mm about the stromal layer.

"Stroma-non-contact" cultures also differed from "stroma-contact" cultures in that a significantly greater number of CFU-GM were recovered from "stroma-non-contact" cultures at weeks 5 and 8 compared with "stroma-contact" cultures (Table 1). This indicates that, in contrast to differentiation-inducing factors, negative regulators of stem cells are either not released or reach the cultured stem cells in lower concentrations in "stroma-non-contact" cultures. Alternatively, direct hematopoietic cell-stroma interaction may actually be required to convey differentiation-inhibiting signals.

EXAMPLE 3

Self-renewal of Stem Cell Population

D. Zipori et al., *Exp. Hematol.*, 6, 816 (1980) have postulated that one of the major roles of stromal tissue may be to maintain the most primitive progenitor ("stem cell") compartment. Removal of the close cell-cell interactions between hematopoietic and stromal cells could, therefore, induce differentiation only and result in an accelerated exhaustion of the stem cell pool. (L. Siminovich et al., *J. Cell. Comp. Physiol.*, 64, 23 (1964)). In order to test this possibility, 6 separate experiments were conducted to compare the absolute number of stem cells capable of initiating long-term bone marrow cultures (LTC-IC) still present after culture of DR$^-$ cells for 5 weeks in "stroma-contact" or "stroma-non-contact" cultures with the absolute number of LTC-IC present in the FACS sorted DR$^-$ population. The results of these experiments are summarized in Table 3, below.

TABLE 3

Stem Cells are Conserved Equally Well When Primitive DR$^-$ Cells
are Cultured in "Stroma-Contact" and "Stroma-Non-Contact" Cultures.

| | ABSOLUTE NUMBER OF LTC-IC SORTED DR$^-$ CELLS$^a$ | | |
|---|---|---|---|
| Experiment | Sorted DR$^-$ cells | "Stroma-contact" | "Stroma-non-contact" |
| 1 | 1/73 | 1/415 | 1/180 |
| 2 | 1/204 | 1/825 | 1/251 |
| 3 | 1/132 | 1/480 | 1/283 |
| 4 | 1/102 | 1/303 | 1/168 |
| 5 | 1/68 | 1/600 | 1/208 |
| 6 | 1/168 | — | 1/349 |
| Mean ± SEM | 1/123 ± 22* | 1/514 ± 89$^\dagger$ | 1/329 ± 28 |

$^a$The absolute number of LTC-IC present in the different cell populations was calculated as the reciprocal of the concentration of test cells that gave 37% negative cultures using the Poisson statistics and the weighted mean method.
** = p = 0.001 and p = 0.009; comparison between day 0 LDA and "stroma-contact" and "stroma-non-contact" cultures respectively.
$^\dagger$ = p = 0.009; comparison between "stroma-contact" and "stroma-non-contact" cultures".

As shown by the data summarized on Table 3, one LTC-IC per 123±22 sorted DR$^-$ cells was present at day 0. When DR$^-$ cells were cultured for 5 weeks in either "stroma-contact" culture (1 LTC-IC per 524±89 initially sorted DR$^-$ cell; p=0.001) or "stroma-non-contact" culture (1 LTC-IC per 239±28 initially sorted DR$^-$ cells; p=0.009) and then assessed for their stem cell content, a decrease in absolute number of LTC-IC was observed. See Table 3. However, the decrease in stem cells capable of initiating long-term in vitro hematopoiesis was significantly greeting in "stroma-contact" than in "stroma-non-contact" cultures (p=0.009). Thus, the present method eliminates the need to provide direct hematopoietic cell-stroma contact to maintain a fraction of pluripotent stem cells which are capable of initiating in vitro hematopoiesis. Surprisingly, culture of normal stem cells separated from the adherent stromal layers results in an increase generation of committed granulocyte-macrophage progenitors and conserves stem cells with long-term in vitro repopulating capacity better than culture of stem cells in direct contact with the stromal layer.

EXAMPLE 4

Stromal-Non-Contact Cultures Plus Added Cytokines

Sorted Lin[31] 34+DR− stem cells were cultured in transwell inserts above irradiated human stromal cells as described in Example 1 (1–5 ml wells). Recombinant human interleuken-3 (5 ng/ml) (IL-3) alone or in combination with 100 ng/ml macrophage inflammatory protein-1α (MIP-1α, R. D. Systems, Minneapolis, Minn.) was added three times per week to the cultures. Additional cultures received 5 ng/ml IL-3 on day 0 and 2 after feeding, and TGF-β (10 ng/ml) on day 4 after feeding. After five weeks, cells recovered from the transwell were enumerated and replated in methylcellulose assay to determine the CFC, or on secondary stromal layers in limiting dilution assay (LDA) to determine the absolute number of LTC-IC. On day 0, freshly sorted DR− cells were also plated in LDA onto stromal layers to provide a measure of the initial LTC-IC. The results of these assays are summarized on Table 4, below.

TABLE 4

| Cytokine | Cell Expansion[1] | CFC[1] | LTC-IC[2] |
|---|---|---|---|
| None | 100 ± 0% | 100 ± 0% | 44 ± 5%¥ |
| IL-3 | 140 ± 480%* | 220 ± 45%* | 52 ± 8%¥ |
| IL-3 + TGF-β | 320 ± 49%¶ | 72 ± 15% | 12 ± 2.4%¥¶ |
| IL-3 + MIP-1α | 1780 ± 480%* | 248 ± 25%¶ | 122 ± 14%¶ |

[1]Compared with cytokine-free cultures. P < 0.05 (*); p < 0.01 (¶).
[2]Compared with day 0 LDA (= 100 ± 0%); p < 0.001 (¥).

As shown by the data in Table 4, IL-3 alone and in combination with MIP-1α, but not with TGF-β, resulted in a significantly greater cell expansion and generation of CFC than did cytokine-free cultures. Culture of DR− cells for five weeks in cytokine-free transwell cultures resulted in a 56% loss of LTC-IC compared with FACS sorted DR− cells (day 0). Addition of IL-3 to transwell cultures also resulted in a small but consistent increase in LTC-IC recovery after five weeks of culture compared with cytokine-free cultures whereas addition of IL-3+TGF-β resulted in a significantly greater loss of LTC-IC. Surprisingly, combined addition of IL-3+MIP-1α resulted in a significantly greater recovery of LTC-IC compared with non-supplemented cultures. Moreover, the absolute number of LTC-IC present in cells recovered from IL-3 and MIP-1α supplemented cultures was either equivalent or greater than that present in the freshly sorted DR− population used to initiate the transwell cultures on day 0 (93%, 135% and 136% of day 0 LDA). In conclusion, this example demonstrates for the first time that stem cells (LTC-IC) can be conserved/expanded in vitro. This requires soluble factors produced by cultured human irradiated stromal cells in combination with IL-3 and MIP-1α.

EXAMPLE 5

Small Scale Ex Vivo Progenitor Expansion System

CD34+HLA-DR− cells were cultured in SCM, prepared as above, with or without supplementation with one or more cytokines, in six-well tissue culture plates (Falcon). 12,000 to 16,000 cells were suspended initially in 2 ml of SCM and incubated at 37° C. in a humidified atmosphere with 5% $CO_2$. Fresh cytokine supplemented medium was added to these cultures as follows: 2 ml on days 3, 5 and 7 and 3 ml on days 10 and 12 after initiation of culture. Cells were harvested after 7 or 14 days of culture. The equivalent of 10,000 originally-plated cells were assayed for LTC-IC using limiting dilution assays as described below and the equivalent of 1000 originally plated cells were assayed for CFC in methylcellulose progenitor culture. Progenitor expansion was evaluated by comparing the number of CFC and LTC-IC present in 1000 cells at initiation of culture with the number of CFC and LTC-IC present in the progeny of 1000 initially-plated cells after 7 and 14 days of culture [Progenitor expansion=CFC present in progeny of 1000 DR− cells at initiation of culture].

1. Stroma-conditioned medium and IL-3 cultures.

Figure 2C:
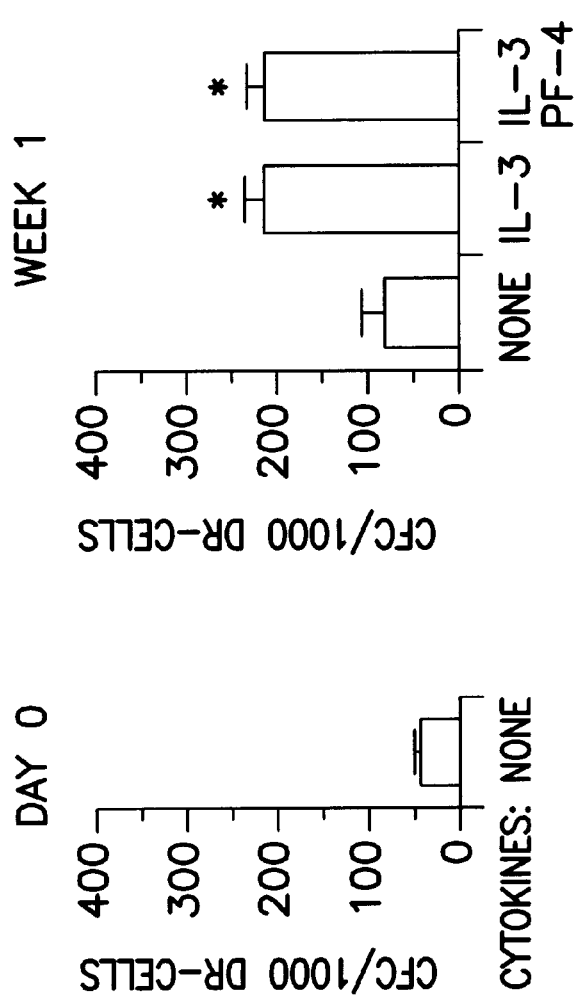
Figure 3A:
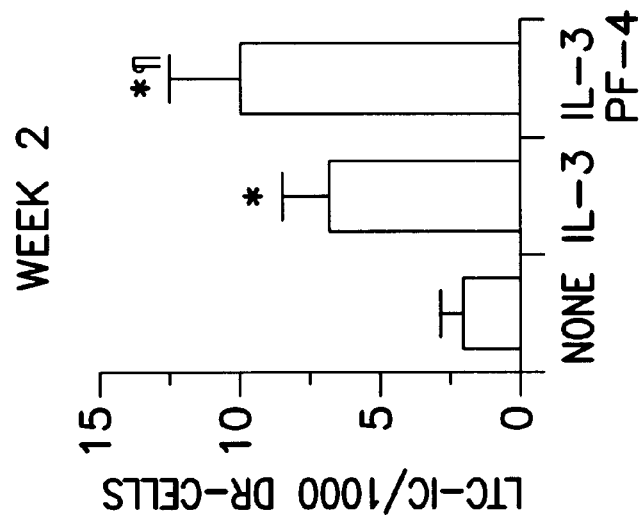
FIG. 3 (Parts A–C) is a graphical depiction of the LTC-IC expansion of DR– cells in cultured in stromal conditioned media+IL-3 and IL-3+PF-4.
Figure 3B:
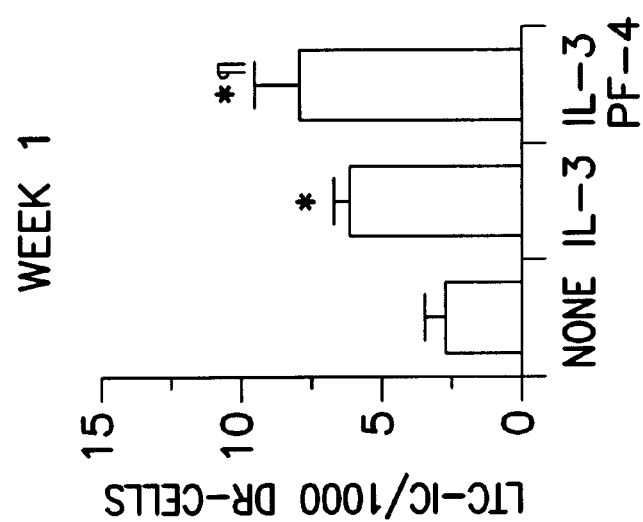
Figure 3C:
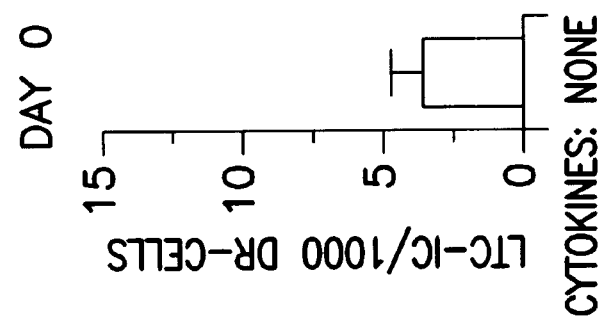

In initial studies normal DR− cells were cultured in SCM with or without supplementation with IL-3 (5 ng/ml) in 6-well tissue culture plates for 1–2 weeks. Additional medium and cytokines were added at 2–3 day intervals as described in the methods. As shown in FIG. 2, culture of DR− cells in SCM without IL-3 resulted in a small but significant expansion of CFC at week 1 and further expansion at week 2 (4.4±1.6 fold expansion after 2 weeks of culture, n=10). Addition of IL-3 to SCM cultures resulted in significantly enhanced expansion of committed progenitors after 7 days and further expansion after 14 days 9.2±2.9 fold expansion after 2 weeks, n=13). As shown in FIG. 3, culture of DR− cells in SCM resulted in maintenance of LTC-IC at 1 and 2 weeks of culture. However, culture of DR− cells in SCM+IL-3 also resulted in a significant increase in the absolute number of LTC-IC at week 1 and week 2 (2.8±0.5 fold expansion after 2 weeks, n=9).

Figure 4B:
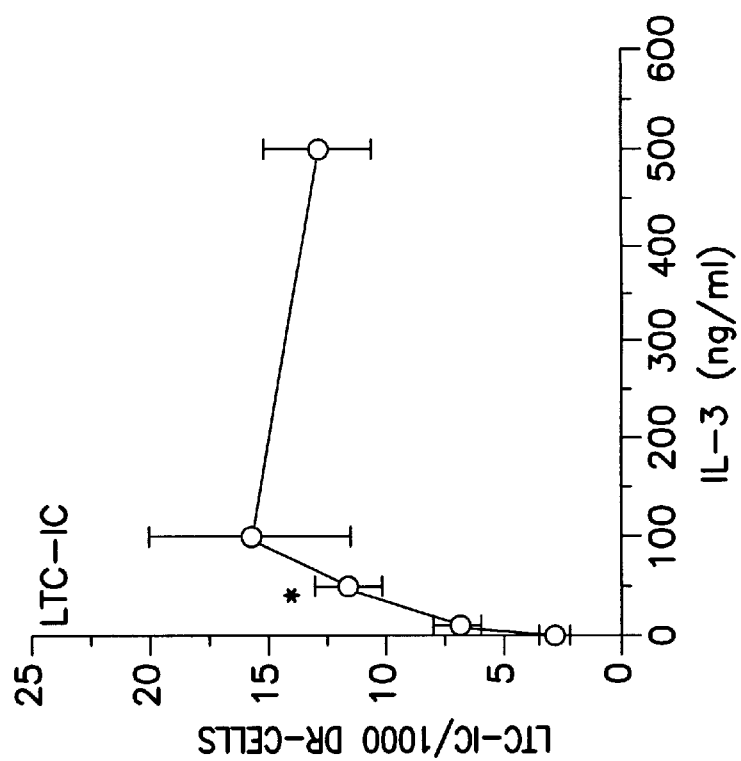
FIGS. 4A and 4B are graphical depictions of the CFC(A) expansion and reduced LTC-IC expansion (B) that results from increasing concentrations of IL3.
Figure 4A:
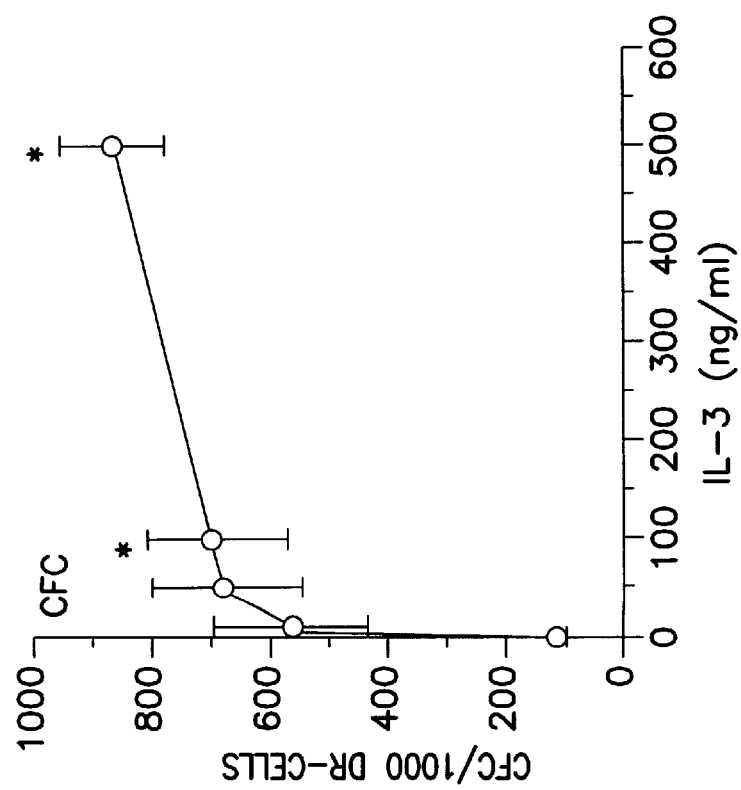

The effect of increasing concentrations of IL-3 on CFC and LTC-IC expansion was also evaluated. As demonstrated in FIG. 4a, significantly increased numbers of CFC were generated when the IL-3 concentration was increased from 5 ng/ml to 500 g/ml. Significantly increased LTC-IC expansion was also observed when the IL-3 concentration was increased from 5 ng/ml to 50 ng/ml and 100 ng/ml. However, a further increase in IL-3 concentration to 500 ng/ml was associated with a decreased recovery of LTC-IC at week 1 and week 2 (FIG. 4b).

2. Addition of PF-4, BB-10010 and MIP-1α to stroma-conditioned medium and IL-3 cultures.

PF-4 is a member of the chemokine family with similar inhibitory effects on hematopoietic progenitor proliferation as MIP-1α. The effect of addition of PF-4 to SCM+IL-3 cultures on normal progenitor expansion was also examined.

Addition of PF-4 did not change CFC expansion in SCM+IL-3 cultures (9.6±2.8 fold expansion after 2 weeks, n=12) (FIG. 2). However, addition of PF-4 to SCM+IL-3 cultures significantly increased LTC-IC expansion compared to cultures of DR[31] cells in SCM+IL-3 alone, both after 1 and 2 weeks of culture (4.2±0.7 fold expansion after 2 weeks, n=9) (FIG. 3).

Figure 5B:
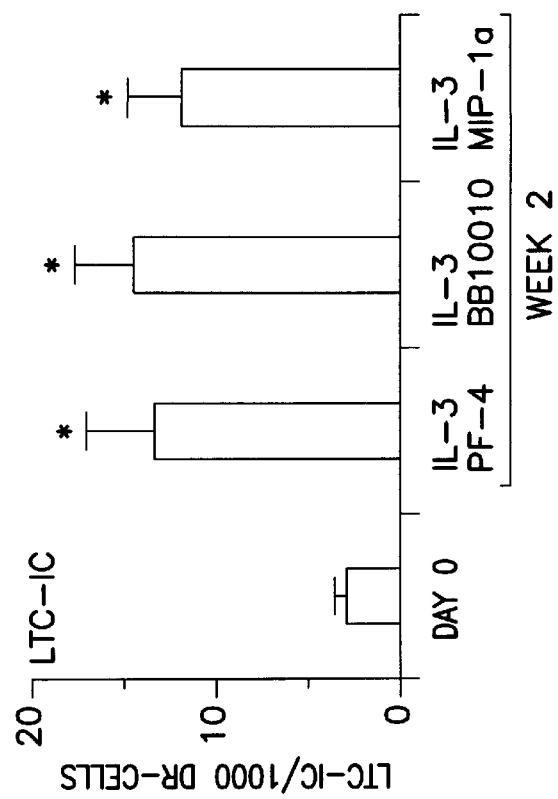
FIGS. 5A and 5B depict that the cytokines PF4, BB10010 and MIP-1α have similar effects on CFC (A) and LTC-IC (B) expansion when added to SCM+IL-3 cultures.
Figure 5A:
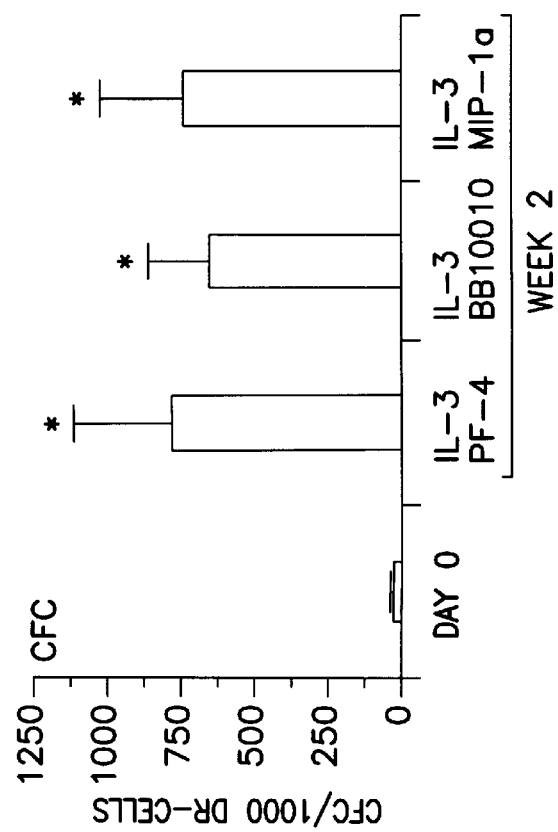

The effect of addition of BB10010, PF-4 and MIP-1α on normal progenitor expansion was also examined. BB10010 is a recombinant variant of MIP-1α, carrying a single amino acid substitution of Asp26>Ala with reduced tendency to form large polymers but with similar effects on hematopoietic progenitors as MIP-1α. See, Hunter et al., *Blood*, 86, 4400 (1995). As shown in FIG. 5, these three chemokines do not differ significantly in their effects on CFC (n=5) and LTC4C expansion (n=4) from DR− cells in SCM+IL-3 cultures. This result indicates that PF-4 and BB10010 have equivalent effects to those of MIP-α in this culture system.

Figure 6B:
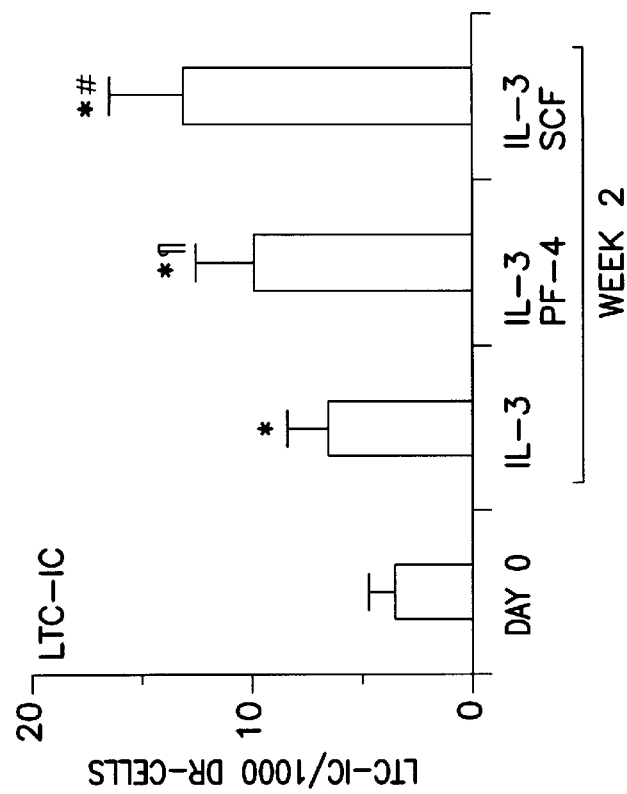
FIGS. 6A and 6B are graphs that depict that the addition of SCF to SCM+IL-3 cultures results in further enhancement of CFC and LTC-IC expansion. Specifically.
Figure 6A:
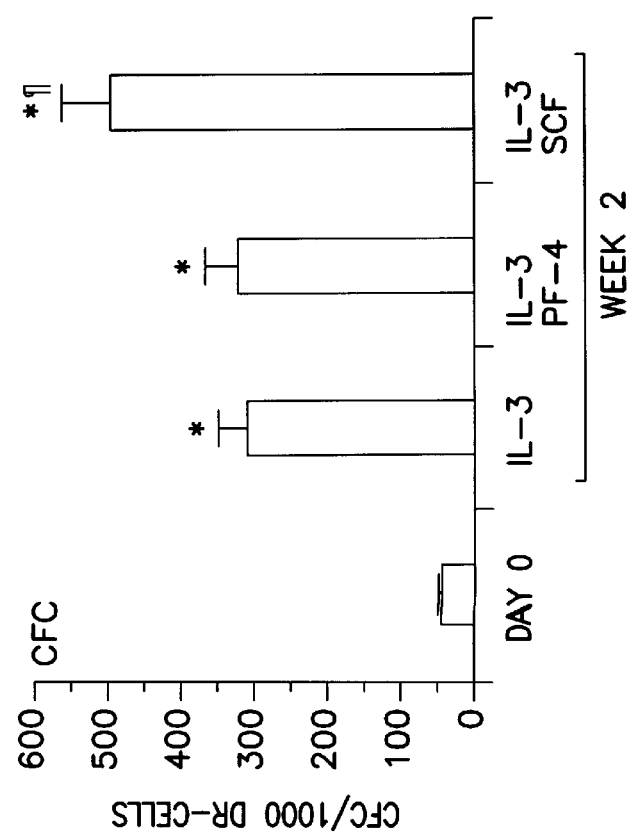

3 Addition of other growth stimulatory cytokines to stroma-conditioned medium and IL-3 cultures Next, the effect of addition of other growth promoting cytokines to SCM+IL-3 (stromal conditioned medium+IL- 3) and SCM+IL-3+PF-4 (stromal conditioned medium+IL-3+PF-4) cultures was evaluated. The addition of the growth promoting early acting cytokines IL-1, IL-6, IL-11 and G-CSF did not significantly increase normal CFC or LTC-IC expansion beyond that observed in SCM+IL-3 cultures or SCM+IL-3+PF-4 cultures (data not shown). However, addition of SCF to SCM+IL-3 cultures significantly increased CFC expansion beyond that observed with SCM+IL-3 alone (12.5±1.7 fold expansion after 2 weeks, n=8) (FIG. 6a). The addition of SCF to SCM+IL-3 cultures also resulted in increased LTC-IC expansion in 5 of 6 experiments ( 5.8±2.5 fold expansion after 2 weeks, n=6) (FIG. 6b). Addition of PF-4 to SCM+IL-3+SCF cultures did not further enhance CFC or LTC-IC expansion (12.8±1.7 CFC expansion and a 2.9±0.6 fold LTC-IC expansion).

In summary, this initial series of experiments demonstrated that SCM and IL-3 alone resulted in significant expansion of primitive and committed progenitors from DR⁻ cells and that this could be further enhanced by addition of SCF.

EXAMPLE 6

Large Scale Ex Vivo Progenitor Expansion System 200,000 to 600,000 CD34$^+$DR$^-$ cells were suspended in 15 ml SCM with IL-3 and cultured in gas-permeable Teflon Fluoropolymer™ bags of 100 cc capacity (American Fluoroseal, Columbia, Md.) at 37° C. in a humidified atmosphere with 5% $CO_2$. Additional medium supplemented with IL-3 was added as follows: 15 ml on days 3, 5 and 7, and 20 ml on days 10 and 12. Cells were removed for progenitor assays after 7 and 14 days of culture. The equivalent of 10,000 initially plated cells were assayed for LTC-IC using limiting dilution analysis and the equivalent of 1000 initially plated cells analyzed for CFC in methylcellulose progenitor culture. Progenitor expansion was evaluated by comparing the number of CFC and LTC-IC present in 1000 cells at initiation of culture with the number of CFC and LTC-IC present in the progeny of 1000 initially-plated cells after 7 and 14 days of culture [Progenitor expansion=CFC present in progeny of 1000 initially-plated DR$^-$ cells after 1 or 2 weeks of culture:CFC present in 1000 DR$^-$ cells at initiation of culture].

Large scale ex vivo culture of DR$^-$ cells in gas-permeable bags mimicked the small-scale cultures described above, and resulted in a 15-fold expansion of CFC (FIG. 7a) and 3-fold expansion of LTC-IC at week 2 (FIG. 7b). As with the small-scale cultures, significantly higher progenitor expansion was seen after 2 weeks of culture compared with 1 week.

In summary, this experiment demonstrates that expansion of DR$^-$ cells in large-scale expansion culture systems employing SCM+IL-3 is similar to that observed in the small-scale expansion system. Although culture in SCM+IL-3+PF-4 or SCM+IL-3+SCF is associated with greater expansion of primitive progenitors, and in the case of SCM+IL-3+SCF of committed progenitors, than SCM+IL-3, SCM+IL-3 was used in the scale up cultures because of the practical difficulties associated with using combinations of cytokines from different sources.

EXAMPLE 7

Long Term Natural Killer (NK)-Cell Culture Initiating Cell (LTNK-IC) Culture

The ability of cultured CD34$^+$DR$^-$ cells to generate NK-cells was also assessed by plating the equivalent of 8000 initially plated DR$^-$ cells in LT-NK cultures. See Taswell, *J. Immunol.*, 126, 1614 (1981). Specifically, CD34$^+$DR$^-$ derived progeny obtained after 14 days of culture in SCM and IL-3 were cultured on allogeneic irradiated stromal layers in 24-well tissue culture plates in a mixture of DMEM/Ham's F12 (GIBCO Laboratories, Grand Island, N.Y., 2:1 vol./vol.) supplemented with 1000 u/ml recombinant IL-2 (a gift from Chiron Co., Berkeley, 100 u/ml penicillin with 100 μg/ml streptomycin (GIBCO), 10% heat inactivated human AB serum North American Biologicals, Miami, Fla.), 24 μM 2-mercaptoethanol, 50 μM ethanolamine, 20 mg/L L-Ascorbic acid and 5 μg/L of sodium selenite ($Na_2SeO_3$). Cultures were maintained in a humidified atmosphere at 37° C. and 5% $CO_2$. Cultures were fed by weekly removal of half the media and replacement with fresh media. At week 4–5, wells were washed thoroughly to harvest cells and analyzed for expansion by evaluating cell counts in a hemocytometer, immunophenotype by FACS analysis and cytotoxicity against the NK sensitive cell line K562 in a 4-hour $Cr^{51}$ release assay.

Immunophenotyping was performed by direct labeling of cells with mouse monoclonal antibodies. FITC- or PE-coupled antibodies were directed at CD3 and CD56 (Becton Dickinson) and FITC- and PE-coupled isotype matched Igs were used as controls. All analyses were performed by a FACS Star$^{PLUS}$ laser flow cytometry system (Becton-Dickinson) equipped with a CONSORT 32 computer system.

Cultured NK populations were tested for cytotoxicity against the NK sensitive cell line K562 (ATCC) in a 4-hour $Cr^{51}$ release assay as described by Miller et al. in *Blood*, 83, 2594 (1994). Effector-to-target ratios ranged from 20:1 to 0.082:1. Target cells were labeled with 200 mCi sodium chromate-$Cr^{51}$ (DuPont, Wilmington, Del.) for 60 to 90 minutes. All determinations were performed in triplicate and percent lysis was determined using the following equation:

$$\frac{\text{Experimental Mean cpm} - \text{Spontaneous Release Mean cpm}}{\text{Total Release Mean cpm} - \text{Spontaneous Release Mean cpm}} \times 100\% = \% \text{ Lysis}$$

Figure 8B:
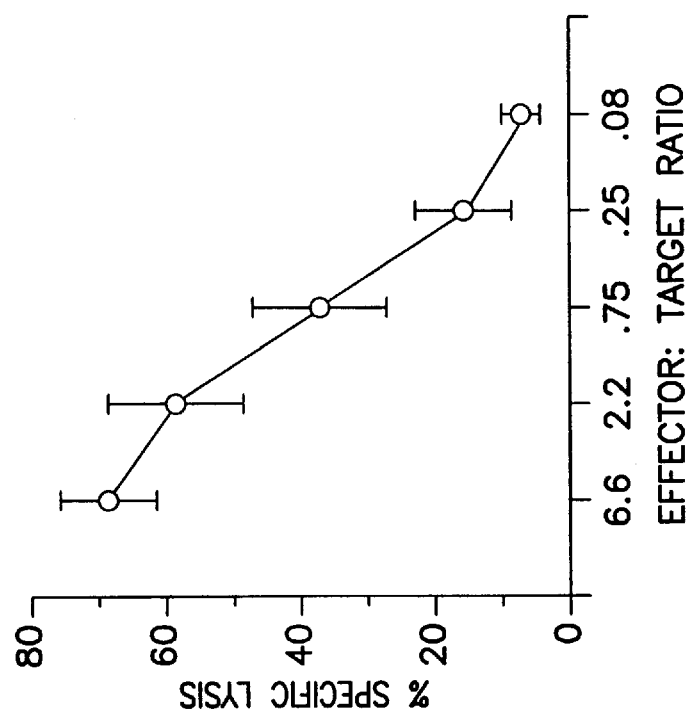
FIGS. 8A and 8B are graphical depictions that NK-cell progenitors are maintained following culture of DR+ cells in SCM+IL-3.
Figure 8A:
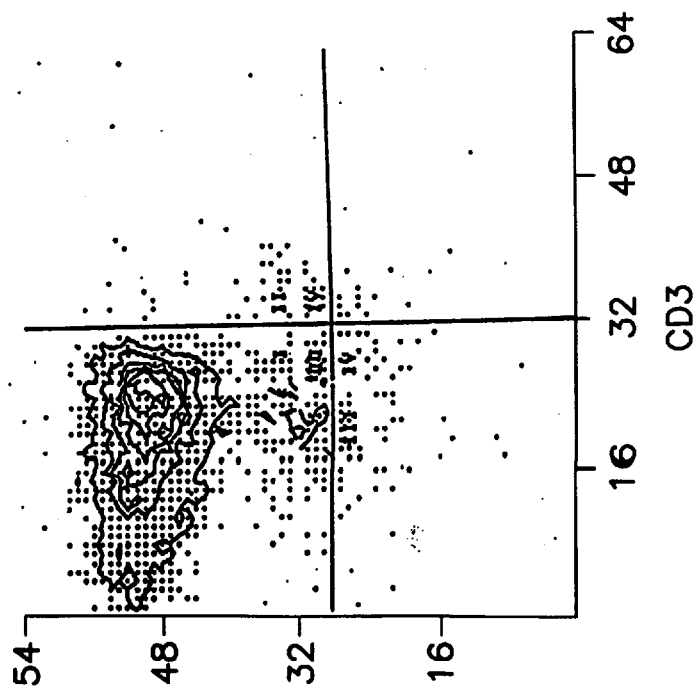

DR$^-$ cell derived progeny recovered at week 2 from large scale SCM+IL-3 cultures were capable of generating NK cells (n=4). Cells recovered at 4 weeks from LT-NK cultures had the characteristic phenotype of mature NK cells (FIG. 8a) and were cytotoxic to the NK sensitive K562 cell line (FIG. 8b). This result indicates that both primitive myeloid and lymphoid progenitors are maintained and/or expanded in these ex vivo expansion cultures.

In summary, this experiment demonstrates here that ex vivo expansion of both CFC and LTC-IC with preservation of lymphoid (NK-cell) progenitors from normal DR$^-$ cells is possible following culture in a simple culture system using stroma-conditioned medium supplemented with a single cytokine, IL-3.

EXAMPLE 8

Expansion of DR$^-$ Cells from Chronic Myelogenous Leukemia Bone Marrow

The ability of SCM+IL-3 cultures to expand CFC and LTC IC from CML BM derived DR$^-$ cells in large scale SCM+IL-3 cultures was assessed. It has recently been shown that it is possible, using FDA approved methods, to obtain pH-negative DR⁻ cells from selected early chronic phase CML patients in quantities (2–4×10$^5$) which are expected to be sufficient to allow for autotransplantation. Verfaillie et al., *Blood,* 87, 4770 (1996). Cells obtained in this manner either freshly sorted and incubated overnight in IMDM+20% FCS at 37° C. in a humidified atmosphere with 5% $CO_2$, or after being cultured in SCM with IL-3 for two weeks, were flash frozen at −70° C. RT-PCR amplification for BCR-ABL and β-actin was performed as described by Verfaillie et al. Verfaillie et al., *Blood* 79, 1003 (1992).

Figure 9B:
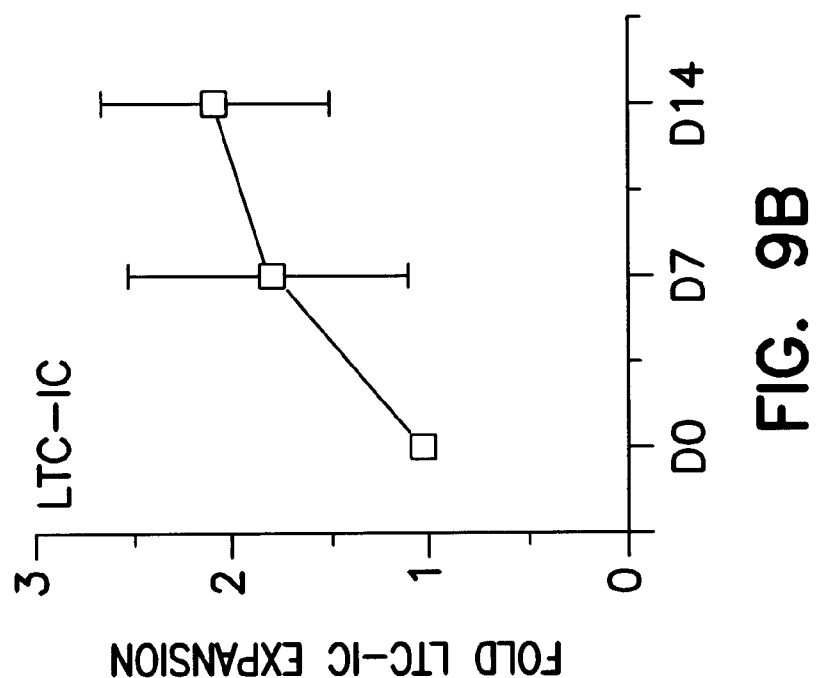
FIG. 9A depicts the assay for CFC in methylcellulose progenitor culture and FIG. 9B depicts the assay for LTC-IC utilizing a limiting dilution assay.
Figure 9A:
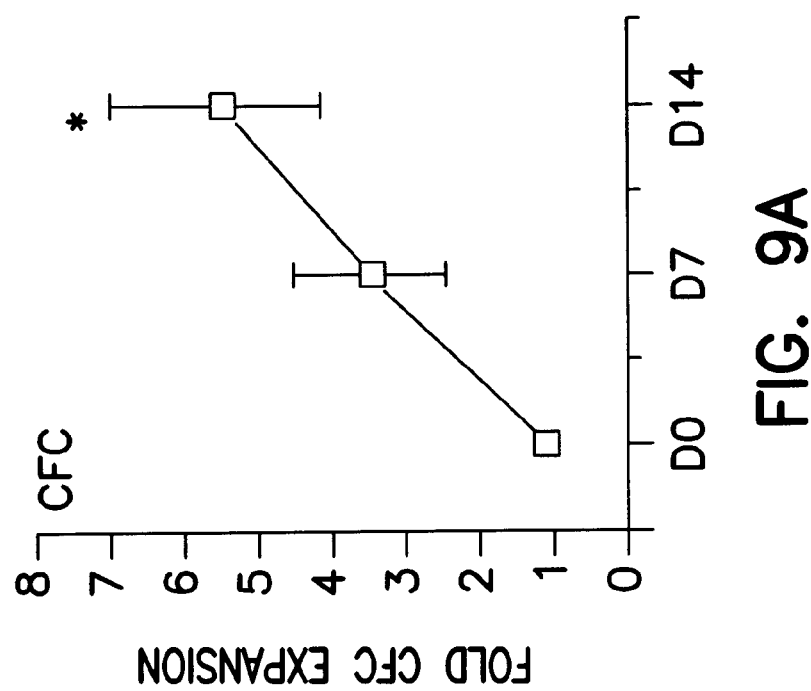
Figure 10:
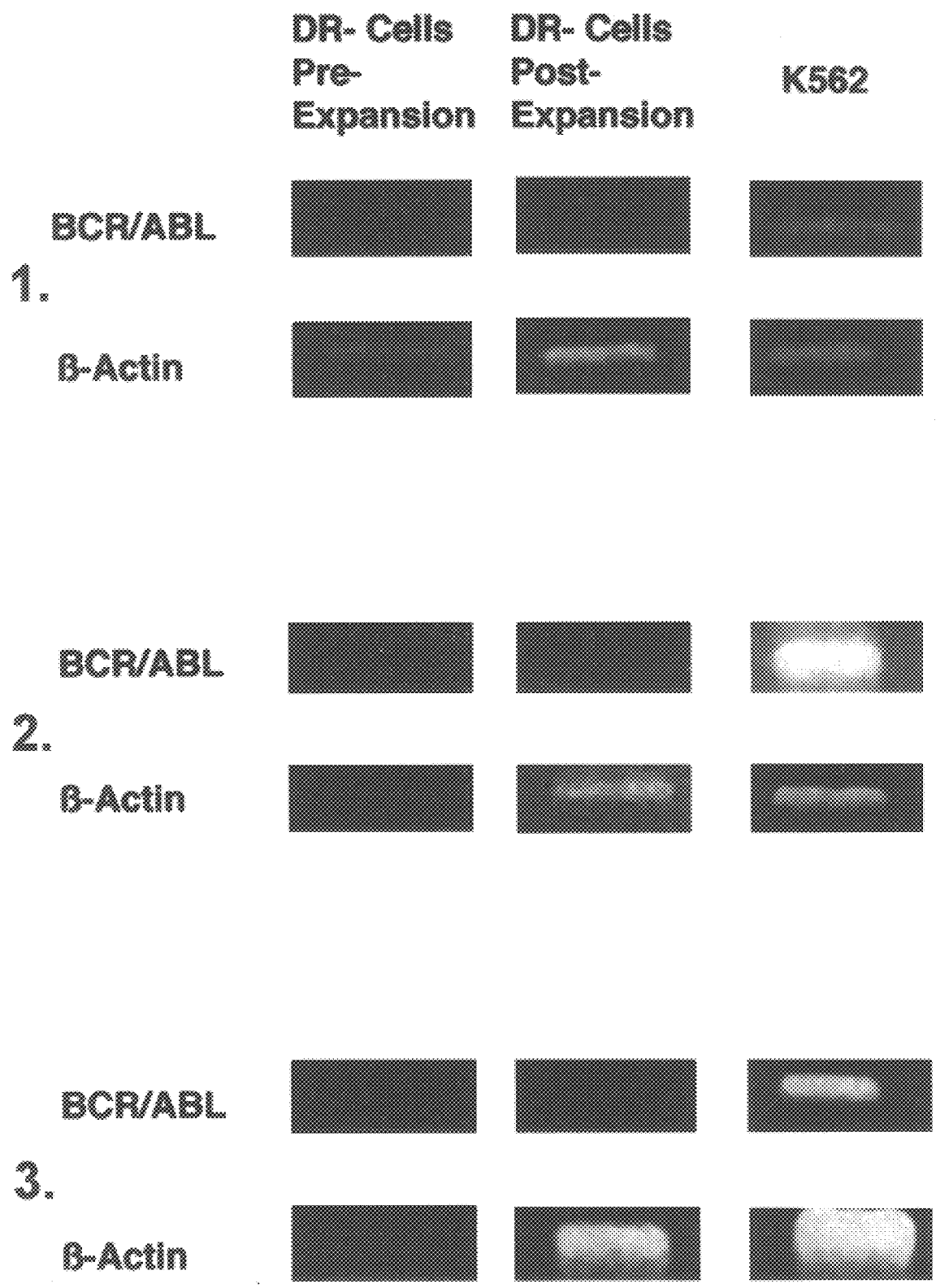
FIG. 10 is a photograph depiction that illustrates that CML bone marrow derived DR– cells remain BCR/ABL negative following SCM+IL-3 culture.

A 5.7±1.4 fold CPC expansion and a 2.1±0.6 fold LTC-IC expansion following culture of CML DR⁻ cells for two weeks in SCM+IL-3 (FIG. 9). CFC expansion following SCM+IL-3 culture was significantly lower for CML DR⁻ cells than for normal DR⁻ cells (p<0.01). In addition, significantly less CFC were present in freshly sorted CML DR⁻ cells compared with normal DR⁻ cells (52.5 CFC/1000 normal BM derived DR⁻ cells and 28.2 CFC/1000 BM derived CML DR⁻ cells, p<0.05). This is likely due to the more stringent sorting criteria used to select BCR-ABL negative DR⁻ cells from CML BM which results in a more profound depletion of committed progenitors. However, LTC-IC expansion from CML and normal DR⁻ cells was not significantly different (2.98±0.7 fold expansion of normal LTC-IC compared with 2.1±1.0 fold expansion of CML CFC). In 3 experiments for which results are available, RT-PCR of DR⁻ cells both prior to initiation of culture as well as following ex vivo expansion culture did not reveal the presence of BCR/ABL mRNA (FIG. 10).

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for culturing hematopoietic cells, comprising: culturing a population of human hematopoietic cells comprising stem cells or committed progenitor cells in a stromal conditioned medium in the absence of stromal cells, wherein the medium comprises an effective added amount of one or more cytokines selected from the group consisting of MIP-1α, IL-3, SCF, BB10010 and PF-4, so that the ability of the stem cells to self-replicate and differentiate is maintained or the ability of the committed progenitors to expand and differentiate is maintained.

2. The method of claim 1 wherein the hematopoietic cells consist essentially of committed progenitor cells.

3. The method of claim 1 wherein the hematopoietic cells comprise stem cells.

4. The method of claim 1 wherein the hematopoietic cells are derived from bone marrow cells.

5. The method of claim 1 wherein the hematopoietic cells are chronic myelogenous leukemia bone marrow cells.

6. The method of claim 1 wherein the hematopoietic cells are derived from peripheral blood or from newborn cord blood.

7. The method of claim 1 wherein the hematopoietic cell population is allogeneic.

8. The method of claim 1 wherein the hematopoietic cell population is autologous.

9. The method of claim 2 wherein the hematopoietic cells consist essentially of natural killer cells.

10. The method of claim 3 wherein the stem cells are CD34⁺.

11. The method of claim 10 wherein the stem cells are Lin⁻CD34$^{+DR-}$.

* * * * *